United States Patent [19]

Culp

[11] Patent Number: 5,411,193
[45] Date of Patent: May 2, 1995

[54] PORTABLE CONTAINMENT DEVICE FOR CONTAMINATED MEDICAL OBJECTS

[76] Inventor: Joel B. Culp, 605 Pioneer Ave., Kent, Ohio 44240

[21] Appl. No.: 116,218

[22] Filed: Sep. 2, 1993

Related U.S. Application Data

[63] Continuation of Ser. No. 749,583, Aug. 26, 1991, abandoned.

[51] Int. Cl.⁶ .............................................. A45F 5/00
[52] U.S. Cl. ................................. 224/252; 224/237; 224/240; 224/245; 224/907; 206/366; 206/370
[58] Field of Search ............... 224/252, 253, 224, 225, 224/228, 235, 236, 237, 240, 242, 245, 907; 206/366, 370

[56] References Cited

U.S. PATENT DOCUMENTS

| | | | |
|---|---|---|---|
| 2,182,738 | 12/1939 | Phillips | 224/225 |
| 2,753,094 | 7/1956 | Haney, Jr. | 224/245 |
| 2,962,155 | 11/1960 | Rusciano | 206/17.5 |
| 2,971,688 | 2/1961 | Akers | 229/38 |
| 2,990,059 | 6/1961 | Hitt | 206/63.2 |
| 3,080,087 | 3/1963 | Cloyd | 220/31 |
| 3,148,822 | 9/1964 | Yochum, Jr. | 229/45 |
| 3,900,550 | 8/1975 | Oliver et al. | 264/320 |
| 4,009,818 | 3/1977 | Rogers | 229/23 R |
| 4,040,419 | 8/1977 | Goldman | 128/215 |
| 4,106,621 | 8/1978 | Sorenson | 206/365 |
| 4,121,755 | 10/1978 | Meseke et al. | 229/38 |
| 4,270,536 | 6/1981 | Lemelson | 128/218 |
| 4,273,123 | 6/1981 | Lemelson | 123/218 N |
| 4,315,592 | 2/1982 | Smith | 229/38 |
| 4,328,904 | 6/1982 | Iverson | 220/256 |
| 4,375,849 | 3/1983 | Hanifi | 206/366 |
| 4,452,358 | 6/1984 | Simpson | 206/366 |
| 4,520,926 | 6/1985 | Nelson | 206/366 |
| 4,679,700 | 7/1987 | Tharrington et al. | 220/337 |
| 4,708,273 | 11/1987 | Grant | 224/252 |
| 4,722,472 | 2/1988 | Bruno | 229/128 |
| 4,743,233 | 5/1988 | Schneider | 604/192 |
| 4,804,090 | 2/1989 | Schuh et al. | 206/366 |
| 4,816,307 | 3/1989 | Honeycutt | 428/34.1 |
| 4,840,272 | 6/1989 | Goldman | 206/365 |
| 4,848,569 | 7/1989 | Leishman | 206/365 |
| 4,900,500 | 2/1990 | Honeycutt | 264/263 |
| 4,969,554 | 11/1990 | Sawaya | 206/370 |
| 5,076,478 | 12/1991 | Unger | 224/253 |
| 5,135,144 | 8/1992 | Blakely et al. | 224/253 |

OTHER PUBLICATIONS

Advertisement for ON•GARD Recapper, ON•GARD Systems, Inc. (1990).
Advertisement for Model 5400 Series Sharps Collectors, Becton Dickinson and Company (1986).
Advertisement for Model 8600 Series Disposal System for Hypodermic Needles and Syringes, Sage Products, Inc. (1981).
Advertisement for Monoject Safety Syringe, Sherwood Medical (1989).
Advertisement for Protectiv I.V. Catheter, Critikon, Inc. (1988).

*Primary Examiner*—Linda J. Sholl
*Attorney, Agent, or Firm*—Howard S. Robbins

[57] ABSTRACT

A portable device (10) for containment of contaminated medical objects (18, 19) during a medical procedure includes a container (12) for receiving the contaminated medical objects (18,19) and having an opening (21) through which the contaminated medical objects (18, 19) are placed by the medical practitioner, and a valve (14) in operative association with the opening (21) in the container for precluding egress of the contaminated medical objects (18,19) placed in the container (12). The container (12) is configured to mount on the medical practitioner during the medical procedure, and further includes an apron (25) with a scalloped interior surface (31) for guiding contaminated medical objects (18, 19) through the valve (14) and into the container (12). A holder (16) includes a clamp (40) for grasping the container (12) and further includes a clip (41) to mount the container on an article of the medical practitioner's clothing during the medical procedure.

13 Claims, 5 Drawing Sheets

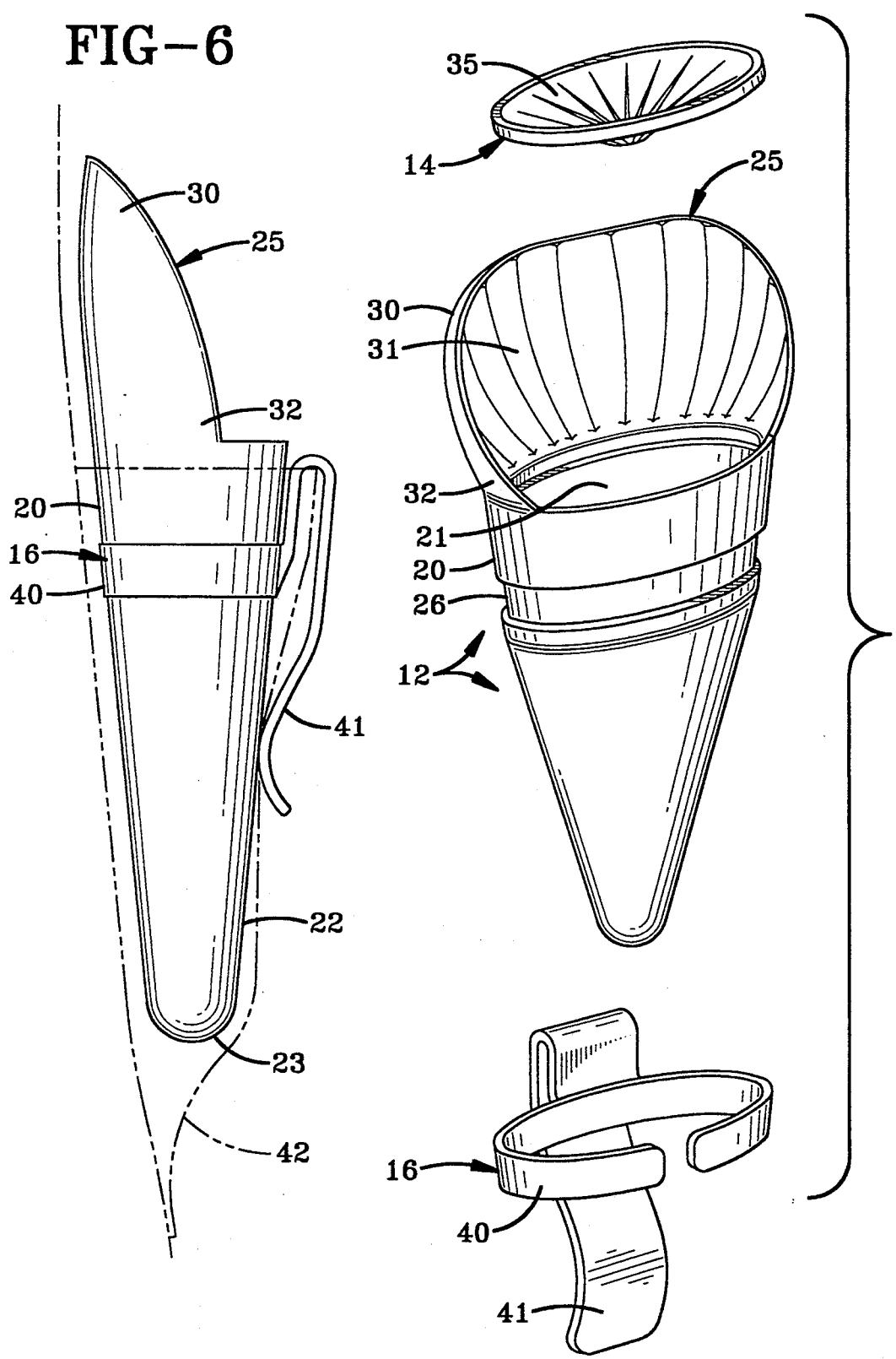

PORTABLE CONTAINMENT DEVICE FOR CONTAMINATED MEDICAL OBJECTS

This is a file wrapper continuation of U.S. Ser. No. 07/749,583 filed Aug. 26, 1991, now abandoned.

TECHNICAL FIELD

The present invention relates generally to devices for receiving and carrying soiled, medical objects. More particularly, the present invention relates to portable devices into which a medical practitioner may place objects such as instruments including needles, syringes and scalpels, and articles including swabs and probes used in and contaminated by medical procedures for safe conveyance to a suitable permanent disposal container.

BACKGROUND ART

Safe disposal of contaminated medical objects has become of utmost concern, especially to the medical community. Accidental needlesticks with contaminated needles account for one of the most serious health risks for medical personnel because of bloodborne pathogens such as AIDS and hepatitis. The magnitude of this sometimes deadly problem may be partly appreciated by the U.S. Government's report in the Federal Register of May 30, 1989 of over 600,000 annual accidental needlesticks.

Medical practitioners are most vulnerable to a needlestick at two critical times during patient care activities: immediately upon the withdrawal of a contaminated needle from a patient and during post-procedure clean-up after the activity is concluded. Almost invariably when a needle is withdrawn the practitioner's attention is divided between needle/syringe disposal and continued patient care. For example, often stabilization and/or pressure must be applied at the site of the intravenous insertion or intramuscular injection, leaving the practitioner tethered to the patient with only one hand free to dispose of the needle/syringe. Frequently the contaminated needle/syringe is simply laid down within the reach of the practitioner's arm. During post-procedure clean-up, at which time the contaminated needle/syringe must be handled a second time, the precise temporary position and orientation may be forgotten or the needle/syringe moved by another, and its position rediscovered by a needlestick.

Vigorous efforts have been made to develop needles and syringes, and disposal devices therefor that are commonly referred to as "sharps" containers or collectors, that reduce the incidence of accidental needlesticks. Such devices may be classified in one of three major categories: needle and syringe containment, needle and syringe destruction, and needle recapping.

Sharps collectors, such as model 5400 series commercially available from Becton Dickinson and Company of Rutherford, N.J., are free-standing or wall-mounted containers that include a "valved" opening to receive the contaminated needle and syringe, a slot to assist in the hands-free removal of the needle from the syringe, and a closure cap. Other sharps containers, such as that described in U.S. Pat. No. 4,969,554, contain a non-valved opening, but include a block of foam to receive and hold the needle. Unfortunately, sharps collectors are very often outside easy arms reach of the practitioner at the time of needle removal, encouraging the temporary needle/syringe placement described above. Even when within reach, the opening may be missed if the practitioner's concentration and visual attention are not directed toward the sharps container. Moreover, under some circumstances free-standing units may require both hands for safe disposal. Also, larger box- or cylindrical-shaped sharps containers invite overfilling and non-uniform orientation of sharp medical objects, resulting in many needlestick injuries.

Needle and syringe destruction devices, such as the Model 8600 commercially available from Becton Dickinson and Company of Rutherford, N.J., cut off the needle near the syringe hub and may optionally cut off the luer adapter from the syringe barrel. These devices require two-hand operation, the practitioner's undivided concentration and attention and, depending on the particular configuration, manual placement of the pieces in suitable sharps collectors or other appropriate medical refuse containers. Furthermore, residual fluids in the syringe or needle have been known to frequently splatter the practitioner when cut.

Another class of devices allow the recapping of needles. Typical of one type of recapping device are the Monoject Safety Syringe with Safety Shield and Needle commercially available from Sherwood Medical of St. Louis, Mo. (shown in U.S. Pat. No. 4,743,233), and the Protectiv I.V. Catheter commercially available from Critikon, Inc. of Tampa, Florida. This first type of device includes a needle cover or shield which is mounted coaxial with the syringe. After use the cover is slid by finger pressure over the syringe needle until an audible click is heard to confirm its locking. During emergency conditions it is very often not possible to hear or feel the interlock engagement click, resulting in cover retraction as soon as one's finger is removed.

Another type of needle recapping device is seen in the ON.GARD Recapper commercially available from ON.CARD Systems, Inc. of Denver, Colo. This is a hand-held unit with a cylindrical grip in which a needle cap is held by a pressure-actuated mechanism. A substantially planer, rectangular plate attached to one end of the grip protects the hand holding the grip while the needle is reinserted into its cap. Here again, successful use of this device requires the practitioner's undivided concentration and attention and works best when done with two hands.

SUMMARY OF THE INVENTION

It is, therefore, an object of the present invention to provide a portable device that is always at hand during a medical procedure and into which a medical practitioner may place contaminated medical objects including instruments such as needles, syringes and scalpels, and articles such as swabs and probes for safe conveyance to a permanent disposal container such as a large, conventional sharps container or a universal hazardous waste bag.

It is another object of the present invention to provide a portable device, as set forth above, that is carried on or in the medical practitioner's clothing.

It is still another object of the present invention to provide a portable device, as set forth above, that operates safely to receive contaminated medical objects, particularly sharp objects as needles and scalpels, without requiring the practitioner's undivided concentration and attention.

It is yet another object of the present invention to provide a portable device, as set forth above, that directs and maintains sharp medical objects placed therein in a uniform orientation.

It is a further object of the present invention to provide a portable device, as set forth above, that operates safely to receive contaminated objects with the practitioner using only one hand, either the right or the left.

It is still a further object of the present invention to provide a portable device, as set forth above, that eliminates the need for double handling of contaminated objects by allowing the immediate and final containment of same.

It is yet a further object of the present invention to provide a portable device, as set forth above, that eliminates the need for post procedure handling of unsecured contaminated objects.

It is an additional object of the present invention to provide a portable device, as set forth above, that eliminates the need to track the temporary position and orientation of contaminated objects.

It is still an additional object of the present invention to provide a portable device, as set forth above, that minimizes the risk of exposure to residual fluids contained within the contaminated objects.

It is yet an additional object of the present invention to provide a portable device, as set forth above, that eliminates the need to recap contaminated needles.

These and other objects and advantages of the present invention over existing prior art forms will become more apparent and fully understood from the following description in conjunction with the accompanying drawings.

In general, a portable device for containment of contaminated medical objects during a medical procedure includes container means for receiving the contaminated medical objects and having an opening through which the contaminated medical objects are placed by the medical practitioner, and a valve in operative association with the opening in the container for precluding egress of the contaminated medical objects placed in the container. The container is configured to mount on the medical practitioner during the medical procedure, and further includes apron means for guiding contaminated medical objects through the valve and into the container. A holder in operative association with the container is provided to mount the container on the medical practitioner during the medical procedure.

BRIEF DESCRIPTION OF THE DRAWINGS

In FIG. 1 the device is depicted clipped to a medical practitioner's belt and is shown containing two contaminated syringes and needles as seen in a partial break-away section thereof.

FIG. 6 is a side elevational view of the exemplary device shown in FIG. 1 depicting its insertion into the pocket of an article of clothing such as a lab coat.

FIG. 7 is an exploded perspective view of the exemplary device shown in FIG. illustrating the three major components of device 10.

PREFERRED EMBODIMENT FOR CARRYING OUT THE INVENTION

Figure 1:
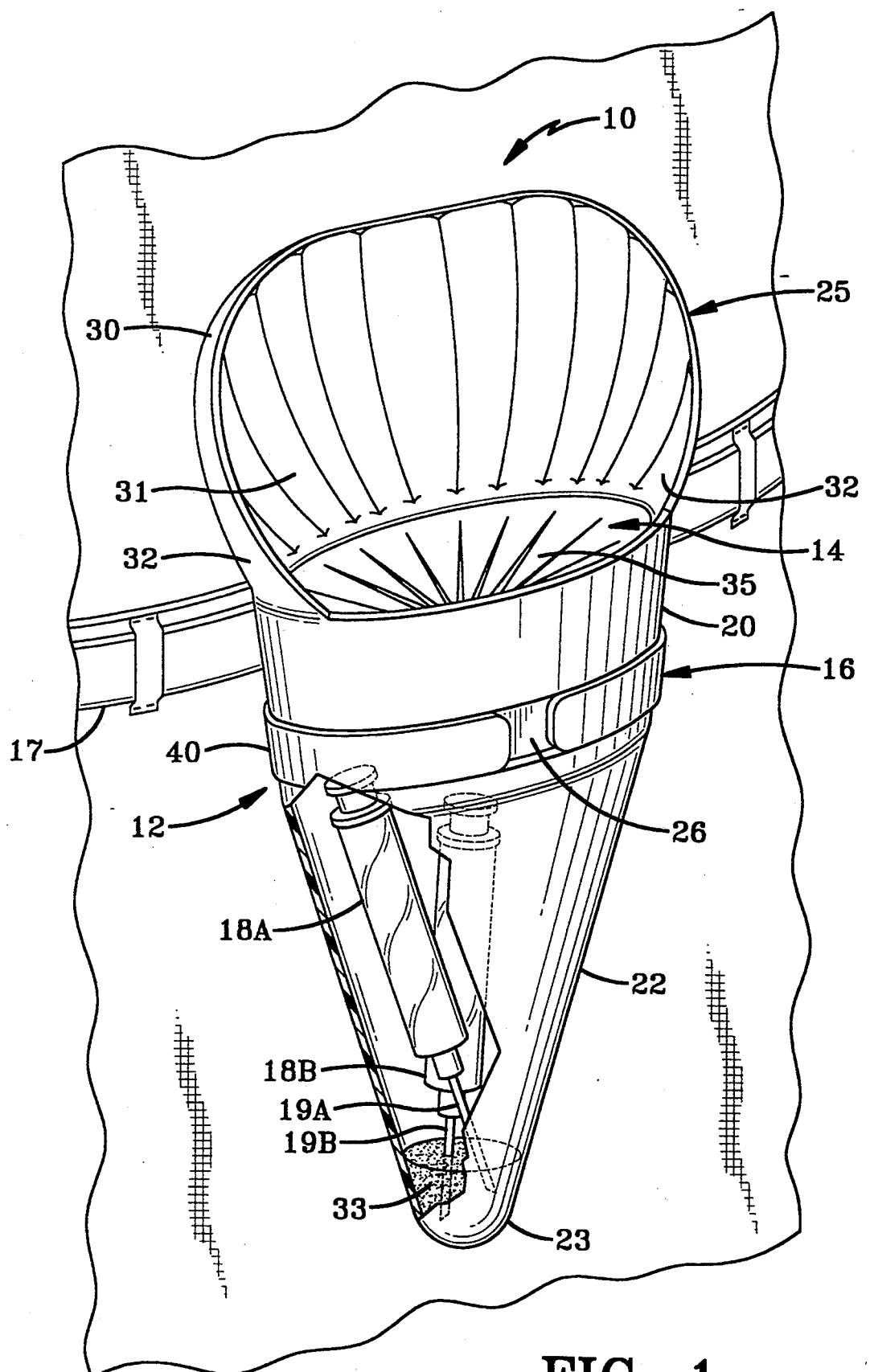
FIG. 1 is a perspective view of an exemplary device in accordance with the present invention.
Figure 2:
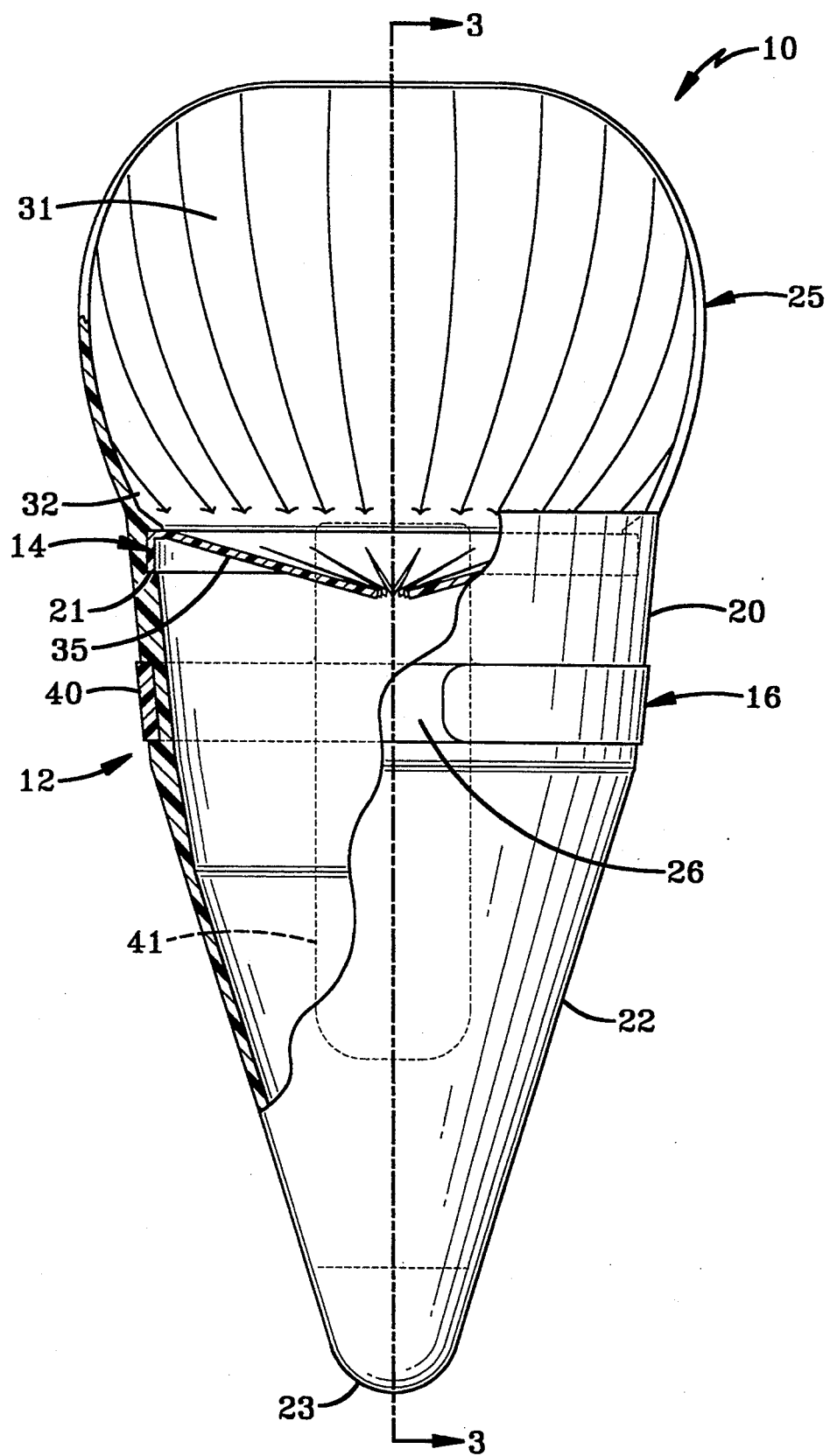
FIG. 2 is a front elevational and partial sectional view of the exemplary device shown in FIG. 1.

FIG. 1 presents in perspective an exemplary portable device in accordance with the present invention, generally indicated by the numeral 10, that is always at hand during a medical procedure and into which a medical practitioner may place contaminated medical objects including instruments such as needles, syringes and scalpels, and articles such as swabs and probes for safe conveyance to a permanent disposal container. Thus, device 10 may be said to be a portable intermediate containment device for contaminated medical objects, and may be called a sharps holster.

Figure 3:
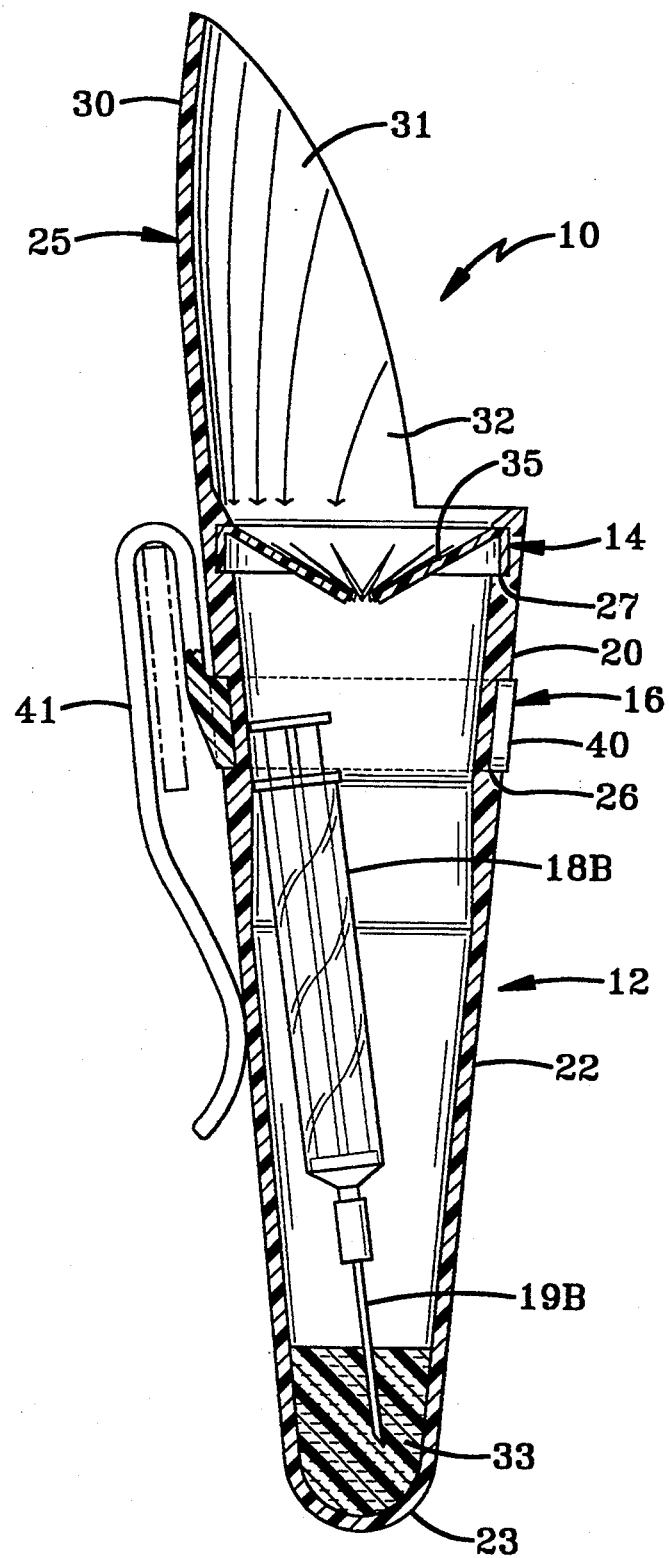
FIG. 3 is a vertical sectional view of the exemplary device shown in FIGS. 1 and 2 taken substantially along the line 3—3 of FIG. 2.
Figure 4:
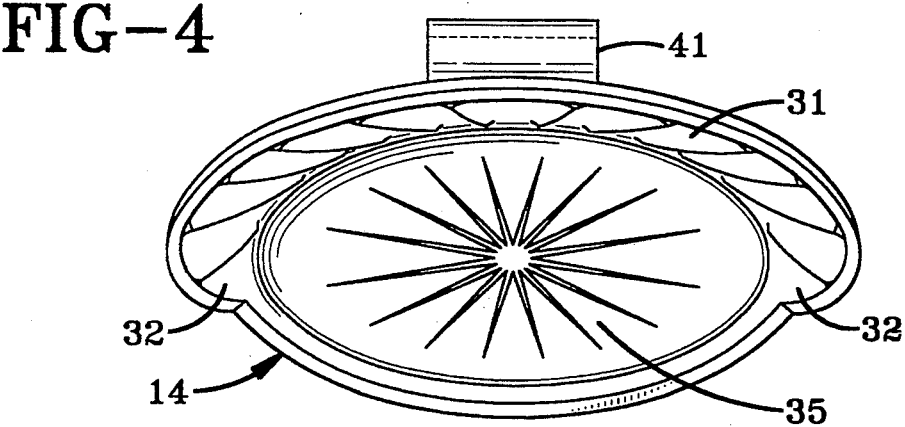
FIG. 4 is a top perspective view of the valve opening to the interior of the exemplary device shown in FIG. 1.

As best seen in FIG. 7, device 10 may be made of three separate components: container 12, safety valve 14 and holder 16. Each separate component may be integrally formed of a suitable material such as a resilient plastic like polyethylene or polypropolene having a wall thickness that may vary to insure it will not be punctured by any contaminated medical object placed therein. In FIG. 1 device 10 is depicted clipped to a medical practitioner's belt 17 and is shown containing two contaminated syringes 18A, 18B and needles 19A, 19B, respectively, as seen in a partial break-away section thereof. Container 12 generally receives and stores the contaminated medical objects. Container 12 includes: a central section 20 preferably of generally oval, substantially fixed cross-section and having an opening 21 at one end thereof; a lower section 22 extending from the opposite end of central section 20 and tapered to a rounded, closed end 23; and an apron 25 extending from the open end of central section 20 opposite that of lower section 22. A recessed collar 26 is formed into the entire outer perimeter of central section 20 just above where central section 20 joins lower section 22. A flange 27, shown in FIG. 3, is formed around the inside perimeter of central section 20 into which safety valve 14 seats as by interference fit and/or interlock engagement, as discussed further herein-below.

Apron 25, as illustrated in FIGS. 1-5, is formed in a flared, half-clamshell with a smooth exterior surface 30 and a scalloped interior surface 31 so that a sharp contaminated medical object like a needle is directed to the center of safety valve 14, greatly minimizing the concentration and attention necessary for the medical practitioner to insure the needle will enter container 12. Indeed, the scalloped interior surface 31 of apron 25 allows the medical practitioner to insert the needle or other contaminated medical object with only one hand. The perimeter of scalloped interior surface 31 may be made visually pronounced as by coloring to further emphasize its spatial position to the medical practitioner and facilitate its location with peripheral vision and minimal concentration during a medical procedure. The outside lower perimeter of scalloped interior surface 31 may be extended to include spatially arcuate side guards 32 as a further safe-guard to insure the needle will enter container 12.

Figure 5:
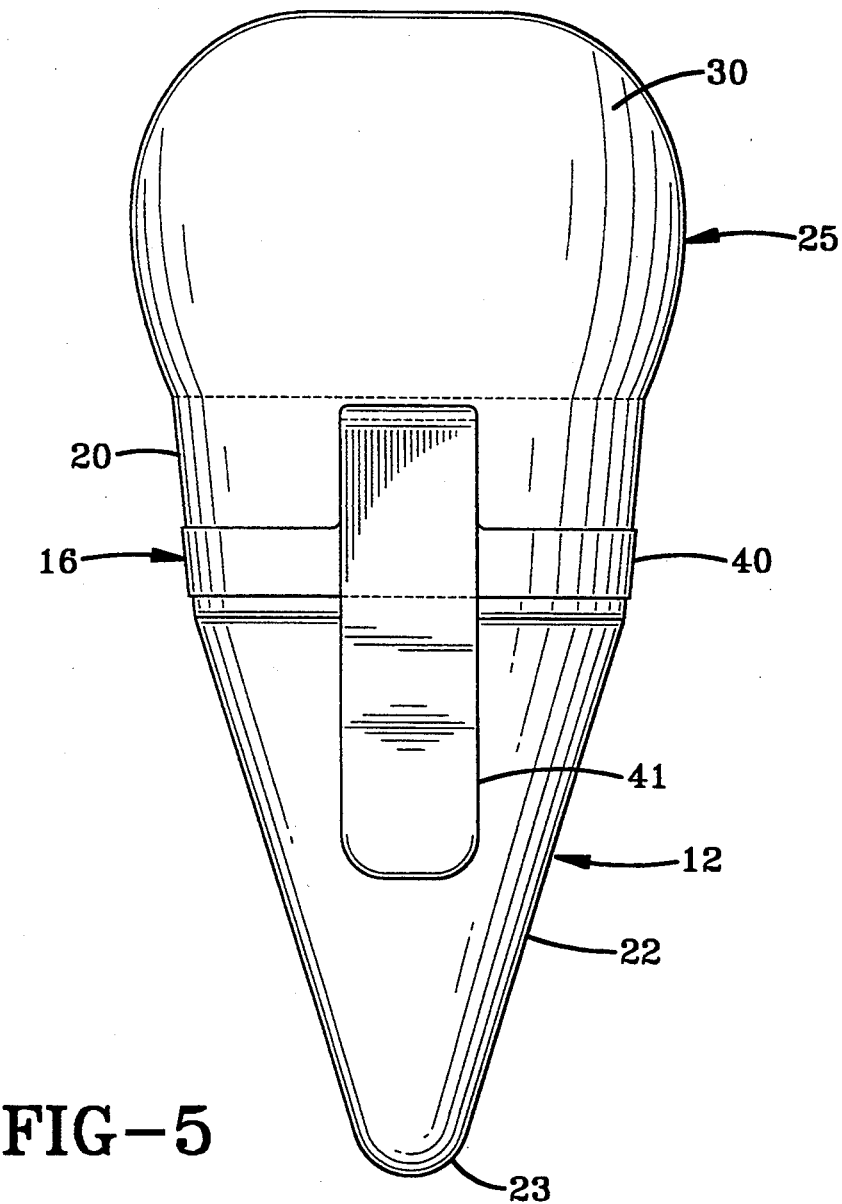
FIG. 5 is a rear elevational view of the exemplary device shown in FIG. 1.

As best seen in FIGS. 1 and 5, the interior of rounded, closed end 23 of lower section 22 may be filled with a stabilizing material 33 such as foam, gel or a soft rubber like silicone suitable to encase the point of any sharp medical object such as a needle, and brace the object within container 12. Stabilizing material 33 may be optionally impregnated with a disinfectant such as chlorine to initiate neutralization of any deleterious agents.

Container 12 is preferably sized to allow collection of all medical objects used in a single medical procedure and thereafter placed in a larger medical refuse container for permanent disposal. Such single use sizing will minimize the possibility of injury from overfilling or contaminated medical objects placed in device 10 from prior procedures, insure contaminants are quickly eliminated and promote further compliance with recommended infectious waste control policies and practices. Since various medical procedures require different quantities and types of objects, device 10 may be made available in a range of sizes.

Safety valve 14, whose outer perimeter is sized and shaped to seat in flange 27, is a generally oval cross-section, one-way pass-through closure for insuring that the contents of central section 20 do not pop-back through the opening in central section 20, also precluding finger contact with the contaminated contents thereof and preventing overfilling and jamming of objects being inserted into central section 20 with objects already inside. Safety valve 14 may use a plurality of flaps 35 hinged to the outer perimeter of safety valve 14 and extending inwardly toward the center of opening 21, each flap 35 having a length that is greater than one half the length of the opening 21 such that flaps 35 would overlap if deformed into the plane of opening 21. A variety of acceptable safety valve designs are known, such as those depicted in U.S. Pat. Nos. 4,328,904 and 4,600,112, and that employed in the model 5400 series Sharps collectors commercially available from Becton Dickinson and Company of Rutherford, N.J.

Holder 16 is preferably a rotatable mechanism for securely grasping container 12 and allowing its mounting to any convenient planar surface such as a medical practitioner's belt, waistband, pocket, or equipment tray or box. Holder 16 includes a substantially oval split clamp 40 for seating engagement with recessed collar 26, and a clip 41 for resilient biased engagement with the selected mounting surface such as the belt 17 shown in FIG. 1 or the pocket 42 shown in FIG. 6. Split clamp 40 is formed to have unbiased major and minor chords that approximate those of recessed collar 26. Thus, when clamp 40 is slid over the tapered lower section 22 of container 12, clamp 40 will snap into seated engagement with recessed collar 26.

Separating the split ends of clamp 40 will allow the withdrawal of container 12 from holder 16, whereupon container 12 and holder 16 may be rotated relative to each other and reengaged with clamp 40 on what was previously the back of container 12. As seen in FIG. 6, in this manner clip 41 may be quickly changed to hook over the front flap of pocket 42.

Operation of device 10 is straightforward and is best understood by reference to FIGS. 1, 6 and 7. Before commencing a medical procedure, the medical practitioner selects a device 10, whose three components in the embodiment described herein have been preassembled at the time of manufacture, of a suitable size for the procedure and inserts clip 41 over belt 17, pocket 42 or a waistband as desired. If necessary clamp 40 may be quickly released from recessed collar 26 and reattached on the other side as described above such that apron 25 will contact the medical practitioner irrespective of the desired placement of device 10.

At those times during the medical procedure when use of a needle, syringe or other medical object is complete, the practitioner simply directs the sharp and/or contaminated end of the object to apron 25, whereupon its scalloped interior surface 31 guides the object through the center of safety valve 14 and into container 12. After the medical procedure is complete, the medical practitioner removes device 10 and deposits it in any suitable hazardous waste container for final disposal.

In addition to the aspects of the present invention noted above, other alternatives and features should now be apparent. For example, while in the preferred embodiment shown and described herein the central section 20 and the lower section 21 are shown as having substantially oval cross-sections, other configurations may be utilized so long as at least one side may lay against the medical practitioner (i.e., there is at least one substantially flat side to container 12) and the configuration allows the desired placement. Other mounting devices such as conventional adhesive pads, non-adhesive Velcro pads, or straps may be used in place of clip 41 in holder 16.

Further, it will be appreciated that the components of device 10 need not be all integrally manufactured. Thus, apron 25 can be made separately and glued or otherwise affixed to the top of central section 20. Safety valve 14 may be left off and stabilizing material inserted and/or impregnated with a disinfectant sometime before use of device 10. Safety valve 14 and flange 27 may be manufactured with small mechanical interlocks that facilitate a positive connection therebetween.

It also now will be understood that the taper of lower section 22 of the end adjacent central section 20 to the rounded, closed end 23, at least facilitates achievement of several significant features. For example, this taper helps keep the sharp ends of needles and scalpels oriented in one direction—down toward end 23, promotes mounting of device 10 on the person of the medical practitioner, and may provide greater structural integrity. The taper also encourages safe, permanent disposal of device 10 by making device 10 easier to pass through the safety valve of a larger sharps container and maintaining the end 23 in a downward attitude if device 10 is thrown in a universal hazardous waste bag.

Inasmuch as the present invention is subject to variations, modifications and changes in detail, some of which have been expressly stated herein, it is intended that all matter described throughout this entire specification or shown in the accompanying drawings be interpreted as illustrative and not in a limiting sense. It should thus be evident that a device constructed and method performed according to the concept of the present invention, and reasonably equivalent thereto, will accomplish the objects of the present invention and otherwise substantially improve the art of containment of contaminated medical objects during conduct of a medical procedure.

I claim:

1. A portable device for containment of contaminated medical objects during a medical procedure, including a container receiving the contaminated medical objects and having an opening through which the contaminated medical objects are placed by the medical practitioner, and a valve in operative association with the opening in said container precluding egress of the contaminated medical objects placed in said container, the improvement comprising:

said container configured to mount on the medical practitioner, said container further including an apron extending in a direction away from said valve for assisting the medical practitioner in locating the opening of said container and for guiding contaminated medical objects into said valve, said apron having a first side and a second side, said first side extending substantially further away from said valve than said second side extends away from said valve; and, a holder in operative association with said container for mounting said container on the medical practitioner.

2. A device as set forth in claim 1, wherein said container has at least one substantially flat sidewall member for lying against the medical practitioner, and said first side of said apron is substantially on the same side of said container as said substantially flat sidewall member.

3. A device as set forth in claim 1, wherein said container is tapered from its opening to a rounded closing at an end opposite thereto.

4. A device as set forth in claim 2, wherein the contaminated medical objects have a sharp end, and said container includes at its end opposite said container opening a stabilizer receiving and bracing said sharp end.

5. A device as set forth in claim 4, wherein said stabilizer includes a disinfectant.

6. A device as set forth in claim 1, wherein said holder includes a clamp engaging the container and a clip for biased engagement with a selected mounting surface.

7. A device as set forth in claim 6, wherein said selected mounting surface for said clip is an article of clothing of the medical practitioner.

8. A device as set forth in claim 1, wherein said first side of said apron is a backstop directing the contaminated medical object into said valve opening.

9. A device as set forth in claim 8, wherein said backstop is scalloped to direct the contaminated medical object into said valve opening.

10. A device as set forth in claim 9, wherein at least the perimeter of said backstop is colored to facilitate location of the area where if contacted by the contaminated medical object directs the same into said valve opening.

11. A device as set forth in claim 1, wherein the contaminated medical objects are contaminated instruments including needles, syringes and scalpels, and contaminated articles including swabs and probes.

12. A device as set forth in claim 3, wherein said container is substantially oval in cross-section.

13. A device as set forth in claim 8, wherein said backstop includes a side guard to direct the contaminated medical object oriented more toward a side of said backstop into said valve opening.

* * * * *